(12) United States Patent  (10) Patent No.: US 8,231,825 B2
Eriksson et al.  (45) Date of Patent: Jul. 31, 2012

(54) METHOD OF PRODUCING A DENTAL PRODUCT

(75) Inventors: Cecilia Eriksson, Djursholm (SE); Petrus Brännvall, Goteborg (SE); Lars Jörneus, Frillesås (SE); Carina Berggren, Torslanda (SE)

(73) Assignee: Nobel Biocare Services AG, Zurich-Flughafen (CH)

( * ) Notice: Subject to any disclaimer, the term of this patent is extended or adjusted under 35 U.S.C. 154(b) by 0 days.

(21) Appl. No.: 12/663,517

(22) PCT Filed: May 28, 2008

(86) PCT No.: PCT/EP2008/004241
§ 371 (c)(1), (2), (4) Date: Jul. 26, 2010

(87) PCT Pub. No.: WO2008/148494
PCT Pub. Date: Dec. 11, 2008

(65) Prior Publication Data
US 2010/0323327 A1  Dec. 23, 2010

(30) Foreign Application Priority Data
Jun. 7, 2007 (EP) ........................................ 7011197

(51) Int. Cl.
*B28B 1/00* (2006.01)

(52) U.S. Cl. .............. 264/678; 264/16; 264/17; 264/18; 264/19; 264/20

(58) Field of Classification Search .............. 264/16–20, 264/677, 678, 497, 605, 652; 29/896.1, 896.11; 433/167, 168.1, 171, 199.1, 201.1, 6, 153, 433/154, 156, 157
See application file for complete search history.

(56) References Cited

U.S. PATENT DOCUMENTS

| | | |
|---|---|---|
| 3,091,014 A | 5/1963 | Smoot et al. |
| 4,362,507 A | 12/1982 | Antonucci |
| 5,080,589 A | 1/1992 | Oden et al. |
| 5,106,303 A | 4/1992 | Oden et al. |
| 5,217,375 A | 6/1993 | Oden et al. |
| 5,283,019 A | 2/1994 | Atwell et al. |

(Continued)

FOREIGN PATENT DOCUMENTS

DE 91 13 284 U1 2/1993

(Continued)

OTHER PUBLICATIONS

PCT/EP2008/004241 International Search Report dated Sep. 16, 2008 issued in the name of Nobel Biocare Services AG.

(Continued)

*Primary Examiner* — Jeffrey Wollschlager
*Assistant Examiner* — Stella Yi
(74) *Attorney, Agent, or Firm* — Knobbe, Martens, Olson & Bear LLP

(57) ABSTRACT

Methods of producing a dental product are disclosed. Certain methods include the steps of providing a pre-sintered blank made from a green body of ceramic material, performing a machining operation on the blank, and subsequently sintering the blank to its final density in a sintering operation performed at a temperature in the range of 1300° C. to 1650° C. The pre-sintered blank that is provided may have a strength in the range of 53-107 MPa.

9 Claims, 4 Drawing Sheets

U.S. PATENT DOCUMENTS

| | | | |
|---|---|---|---|
| 5,342,201 A | 8/1994 | Oden | |
| 5,350,551 A | 9/1994 | Shino | |
| 5,565,152 A | 10/1996 | Od en et al. | |
| 5,775,912 A | 7/1998 | Panzera et al. | |
| 5,788,498 A | 8/1998 | Wohlwend | |
| 6,106,747 A | 8/2000 | Wohlwend | |
| 6,133,174 A | 10/2000 | Brodkin et al. | |
| 6,354,836 B1 * | 3/2002 | Panzera et al. | 433/215 |
| 6,884,969 B1 | 4/2005 | Brach et al. | |
| 7,604,759 B2 | 10/2009 | Gubler et al. | |
| 2002/0125619 A1 | 9/2002 | Bodenmiller et al. | |
| 2004/0119180 A1 | 6/2004 | Frank et al. | |
| 2005/0023710 A1 | 2/2005 | Brodkin et al. | |
| 2006/0082033 A1 | 4/2006 | Hauptmann et al. | |
| 2006/0168815 A1 | 8/2006 | Saliger et al. | |
| 2007/0056467 A1 * | 3/2007 | Panzera | 106/35 |

FOREIGN PATENT DOCUMENTS

| | | |
|---|---|---|
| DE | 199 04 523 A1 | 8/2000 |
| DE | 103 25 524 A1 | 4/2004 |
| EP | 0 774 933 B1 | 5/1997 |
| EP | 0 943 295 A | 9/1999 |
| EP | 1 396 237 A | 3/2004 |
| EP | 1 535 587 A1 | 6/2005 |
| GB | 1 440 331 | 6/1976 |
| GB | 2 064 737 A | 6/1981 |
| WO | WO 01/12097 | 2/2001 |
| WO | WO 2004/086999 A1 | 10/2004 |
| WO | WO 2006/025778 A1 | 3/2006 |
| WO | WO 2006/031096 A1 | 3/2006 |
| WO | WO 2006/079459 A | 8/2006 |
| WO | WO 2007/147549 A | 12/2007 |

OTHER PUBLICATIONS

PCT/EP2008/010645 International Search Report dated Mar. 19, 2009 issued in the name of Nobel Biocare Services AG.

Kennard, F., "Cold Isostatic Pressing," in *Engineered Materials Handbook*, vol. 4: Ceramics and Glasses (ASM International, 1991) pp. 147-151.

Extended European Search Report in European Application No. 07011197.6 dated Oct. 24, 2007.

PCT/EP2008/004245 International Search Report dated Aug. 7, 2008 issued in the name of Nobel Biocare Services AG.

Communication of a Notice of Opposition for counterpart EP Application No. 07011197 (EP Patent No. 2000109) dated Feb. 14, 2012 (received Feb. 17, 2012).

X. Balmes, "From dream to reality," in Spectrum Dialogue, vol. 6, No. 1, Seiten 52-66, Januar 1997.

Erklärung Wilfried Tratter vom 2. Februar 2012.

S. Opferkuch in dental-labor, LIII, Heft Dec. 2005, Seiten 1825-1836.

* cited by examiner

METHOD OF PRODUCING A DENTAL PRODUCT

CROSS-REFERENCE TO RELATED APPLICATIONS

This application is a national stage application under 35 U.S.C. §371 of PCT Application No. PCT/EP2008/004241, filed on May 28, 2008, which published in English as WO 2008/148494 A1 on Dec. 11, 2008 and which claims priority benefit of European Patent Application No. 7011197-6, filed on Jun. 7, 2007, the entire contents of which applications and publication are herein incorporated by reference in their entirety.

BACKGROUND

1. Field of the Invention

The present application relates to a method of making a dental product, in particular a dental bridge, in which a blank made of a pre-sintered green body is first machined and subsequently sintered to its final density.

2. Description of the Related Art

A known method of making dental prostheses includes pressing a ceramic powder into a green body that is subsequently subjected to a pre-sintering operation in which the green body becomes a somewhat more solid blank but does not reach its final density. A machining operation is performed on the blank in order to form a dental prosthesis and the so formed product is then sintered to its final density. United States patent application publication US 2004/0119180 A1 discloses a method in which a pre-sintered blank is machined by a milling process and dense-sintered in a temperature range of from 1200 to 1650° C. According to US 2004/01 19180, the pre-sintered blank has a "green strength" of from 31 MPa to 50 MPa. It is further indicated that blanks having a strength that lies outside the chosen range of 31 to 50 MPa do not yield useful results. According to the publication in question, blanks having a strength below the indicated range may break during milling while higher strengths result in hard blanks that cannot be machined using customary machining processes. It is an object of the present application to provide an improved method of making dental prostheses as will be explained in the following.

SUMMARY

The present application relates to a method of producing a dental product. In certain embodiments, the method comprises the steps of providing a blank made from a green body of ceramic material, performing a machining operation on the blank, and subsequently sintering the blank to its final density. The blank is sintered to its final density in a sintering operation performed at a temperature from 1300° C. to 1650° C. According to certain embodiments of the invention, the pre-sintered blank that is provided has a strength of 53-74 MPa or, possibly, a strength in the range of 56-65 MPa.

During the machining operation, the blank is transformed into a shape that may comprise a bridge structure and a support body that is linked to the bridge structure. In certain embodiments, the blank is preferably formed to an enlarged bridge structure with at least one retaining section between the support body and bridge structure. In some embodiments, the bridge structure, retaining element and the support body are machined from one blank. In some embodiments, the support body is linked to the bridge structure by at least one retaining section that extends from the support body to the bridge structure. During the machining operation, the blank may be machined to a shape where the bridge structure forms an arch and several retaining sections connect the support body to the bridge structure. In certain embodiments, the blank may then be sintered to its final density standing on the support structure while the at least one retaining section holds the bridge structure connected to the support body. In this way, the at least one retaining section may serve to hold the bridge structure in a correct position during sintering. In this way, precision during manufacturing may be improved.

Optionally, there may be several retaining sections and the retaining sections, or some of the retaining sections, may be machined to have the shape of spokes that extend from a common hub in the support body to the bridge structure.

A pre-sintered blank according to certain embodiments of the invention may have a density in the range of 2.9 g/cm-3.8 g/cm$^3$. In some embodiments of the invention, the pre-sintered blank may have a density in the range of 3.0 g/cm$^3$-3.5 g/cm$^3$.

The blank may be a blank that has been made of a green body of zirconium oxide that has been isostatically pressed and subsequently pre-sintered at a temperature in the range of 800° C.-1100° C. In many cases, pre-sintering may be performed at a temperature in the range of 1000° C.-1100° C. The green body may have been isostatically pressed at a pressure of 200 MPa-300 MPa. After machining, the blank may be sintered in certain embodiments to a final density of 6.00 g/cm$^3$-6.09 g/cm$^3$.

DETAILED DESCRIPTION

Figure 1:
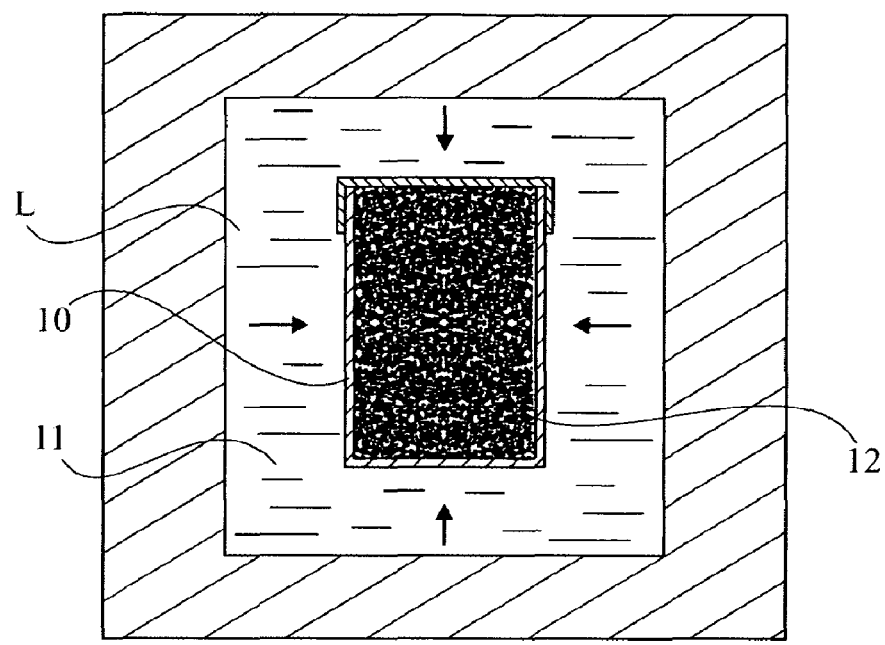
FIG. 1 shows how a ceramic material is pressed to a green body in certain embodiments.
Figure 2:
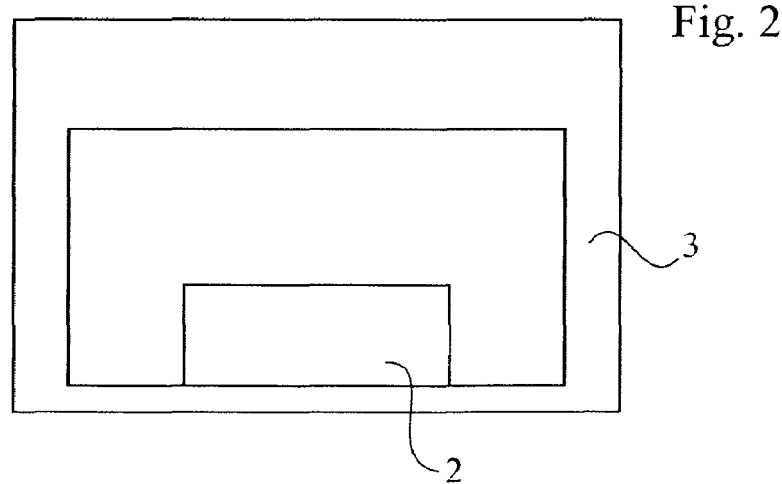
FIG. 2 is a schematic representation of how a green body or a machined blank may be placed in a furnace.

With reference to FIG. 1, a green body of ceramic material may be produced by subjecting a ceramic powder to pressure. In FIG. 1, it is schematically indicated how powder 12 may be placed in a mold 10 which may be made of a flexible material such as rubber. The powder material 12 may be, for example, zirconium oxide powder in the shape of powder granules. The mold 10 which has been filled with powder 12 is placed in a chamber 11 that is filled with a liquid L. The liquid L is pressurized and the powder 12 is subjected to such a high pressure that the powder 12 becomes a solidified green body. The pressure used to transform the powder 12 into a green body may be, for example, 200 MPa but higher pressures may also be used. For example, the pressure used may well be in the range of 200 MPa-300 MPa but higher pressure levels could also be considered. The green body 2 that is formed during pressing may be placed in a sintering furnace 3 as schematically indicated in FIG. 2. In the sintering furnace, the green body 2 is subjected to a pre-sintering operation. The pre-sintering operation in certain embodiments should be understood as an operation where the sintering is interrupted before the green body 2 has reached its final density. The green body 2 typically contains binder material that may be organic and which contributes to holding the green body together. When the green body 2 is heated in the sintering furnace 3, the initial effect will typically be that organic binder material is vaporized and starts to leave the green body 2. During this process, the strength of the green body 2 may actually decrease since the binder material has contributed to holding the green body 2 together. In order to avoid rapid vaporization, the green body 2 may be heated relatively slowly to give the vaporized binder material time to leave the green body without any sudden bursts that could harm or deform the green body 2. The rate of heating may of course vary depending on the properties of each green body 2 but a heating rate of 0.1-1° C./minute can be mentioned as an indication of what may be a possible heating rate in many cases. Here, it may be added that the heating rate need not necessarily remain the same during the entire heating process. Additionally, the temperature can be held constant at different temperature levels during pre-sintering, e.g. to have a controlled vaporization. The temperature used during the pre-sintering process may reach a final level in the range of 800° C.-1100° C. or somewhat higher. As the pre-sintering process continues in certain embodiments, the small particles in the powder will start to form connections to each other and the strength of the green body 2 increases. In this process, the green body 2 is transformed into a pre-sintered blank 1. In certain embodiments, the sintering is interrupted and the blank 1 is taken out of the furnace 3 before it has reached its final density.

Figure 3:
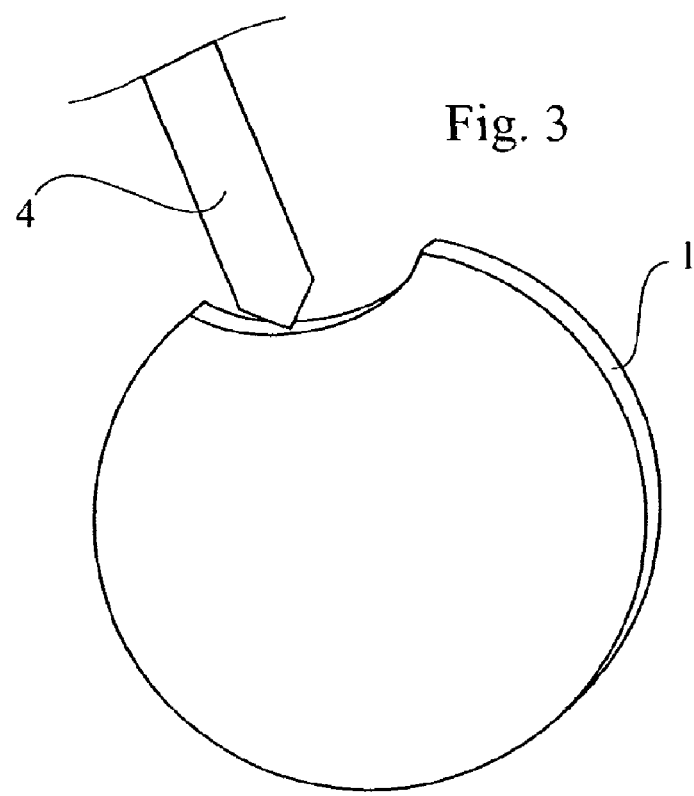
FIG. 3 is an example schematic representation of how a pre-sintered blank is subjected to a machining operation.

The blank 1 will now be sufficiently strong to be machined without falling into small pieces but yet it is still soft that it can easily be subjected to a machining operation. At this stage, the blank 1 is subjected to a machining operation to form something that may later become a dental product, such as a dental bridge. In FIG. 3, it is schematically indicated how a pre-sintered blank 1 may be machined with a tool 4. The machining operation may include, for example, milling, grinding, turning or drilling.

Figure 4:
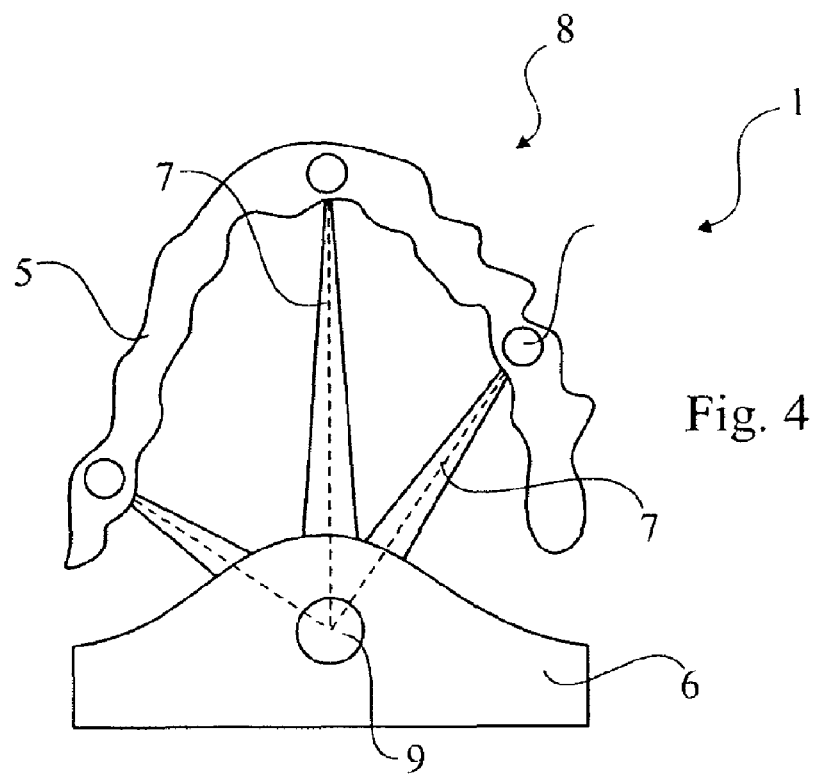
FIG. 4 shows an example of a possible shape for a blank after machining.
Figure 5:
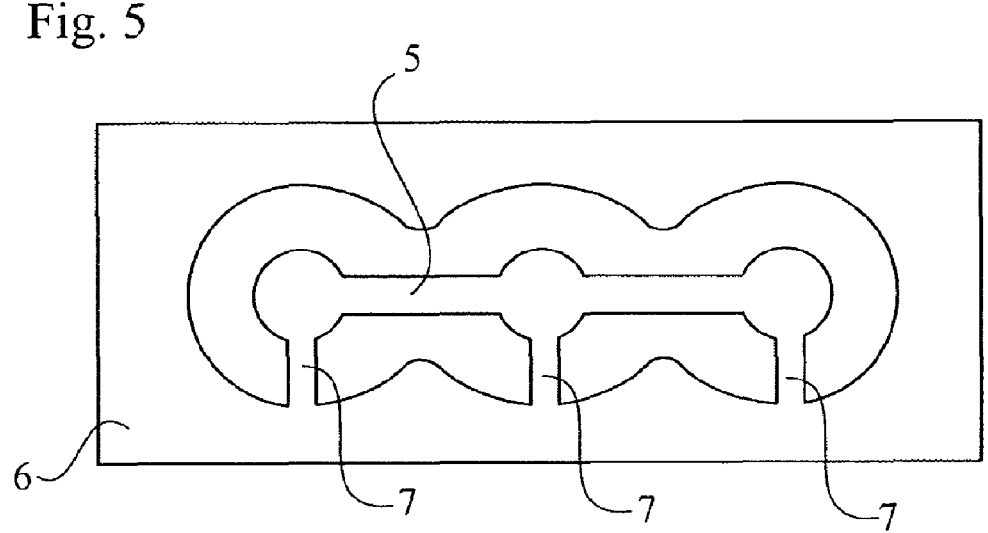
FIG. 5 shows yet another example of a possible shape for a blank after machining.
Figure 6:
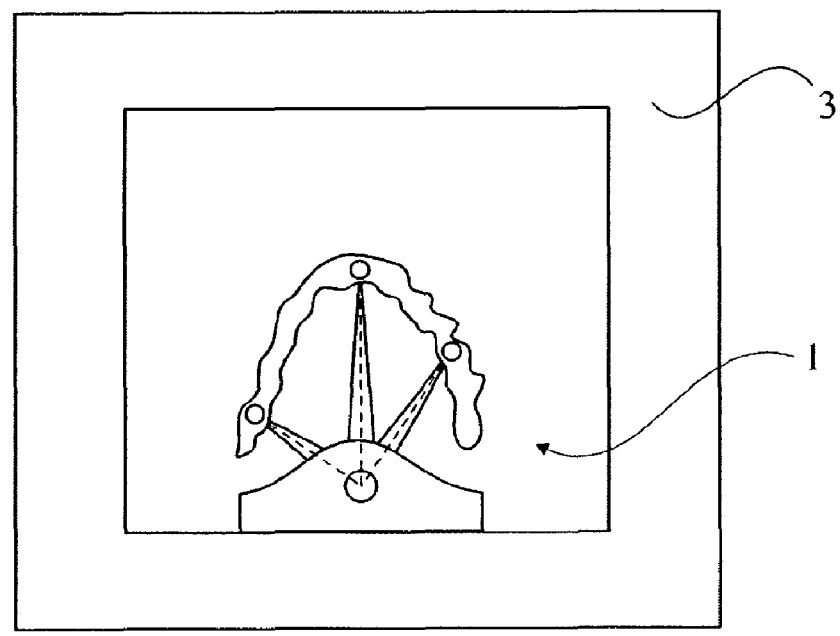
FIG. 6 is an example schematic indication of how a blank that has been machined is placed in a furnace for final sintering.

In FIG. 4 and FIG. 5, examples of a blank 1 are shown where the blank 1 has been shaped by a machining operation into the shape that the blank 1 will have during the final sintering. When describing FIG. 4 and FIG. 5, reference will be made to a bridge structure. However, this is only for convenience and should not be construed as limiting, rather as an example. In the embodiments shown in FIG. 4 and FIG. 5, the blank 1 has been shaped in the machining operation into a shape comprising a bridge structure 5 and a support body 6. The support body 6 is linked to the bridge structure 5 by retaining sections 7 that extend from the support body 6 to the bridge structure 5. During final sintering, the blank 1 may be placed standing on the support body such that the bridge structure 5 is held by the retaining section 7 or retaining sections 7. In this way, the bridge structure 5 need not lie directly on the bottom of the sintering furnace. As a consequence, the risk that frictional forces will act on the bridge structure during final sintering may be reduced. In this context, it should be understood that in certain embodiments, the blank 1 will shrink to some extent during final sintering. This may result in frictional forces between the blank 1 and the surface on which it is resting. Such frictional forces may cause deformation of the blank 1 and the attached dental product, e.g. a bridge. This risk is reduced by the use of the at least one retaining section 7. As indicated in FIG. 4, the bridge structure 5 may be shaped to form an arch 8 while the at least one retaining section 7 may take the form of several spokes that extend from a common hub 9 located in the support body 6 and that extend to the bridge structure 5. Such a shape provides effective support for the bridge structure 5 during final sintering. In FIG. 6, it is schematically indicated how the machined blank 1 may be placed in a furnace 3 for final sintering. Final sintering may be performed at a temperature in the range of 1300° C.-1650° C.

In order to obtain an effective machining operation in certain embodiments, the blank 1 should have such a strength that it will hold together during machining instead of breaking into parts. However, in these embodiments, it should still be soft that it can be shaped relatively quickly and without excessive wear on the tool(s) 4 that is (are) used during machining. It has previously been thought that the blanks 1 should have a strength in the range of 31-50 MPa. Surprisingly, it has now been found that in certain embodiments, the machining operation actually works better if the blanks have a strength that is higher than 31-50 MPa. During laboratory trials, selected blanks of pre-sintered zirconium oxide were machined and the results were compared. The pre-sintered blanks used in the test had a strength ranging from about 40 MPa up to 107 MPa. It was found that the blanks having a strength below 50 were actually too soft and brittle to be really suitable for machining. This also made it more difficult to perform effective and accurate machining on the blanks. However, blanks having a strength from 53 MPa and above were found to be sufficiently solid to permit fast machining without breaking. It was found that, in some cases, the strength may actually be up to 107 MPa although in some cases, a blank at such a high strength could not be machined as easily as a blank having a strength of, for example, 65 MPa. In many cases, a suitable value for strength may be in the range of 53 MPa-74 MPa while 56 MPa-65 MPa may be preferred in some cases where it is important that machining can be performed quickly on a blank having sufficient strength. In certain embodiments, such a blank may, e.g., be suitable for machining retaining sections 7 having sufficient strength during final sintering.

The pre-sintering may be performed at temperatures in the range of 800° C.-1100° C. It should be understood that the choice of temperature may depend to a large degree on the time available for pre-sintering. If the pre-sintering is performed over a relatively long period, a lower temperature may be used, e.g. 800° C. If the time available for pre-sintering is shorter, a higher temperature may be used.

Figure 7:
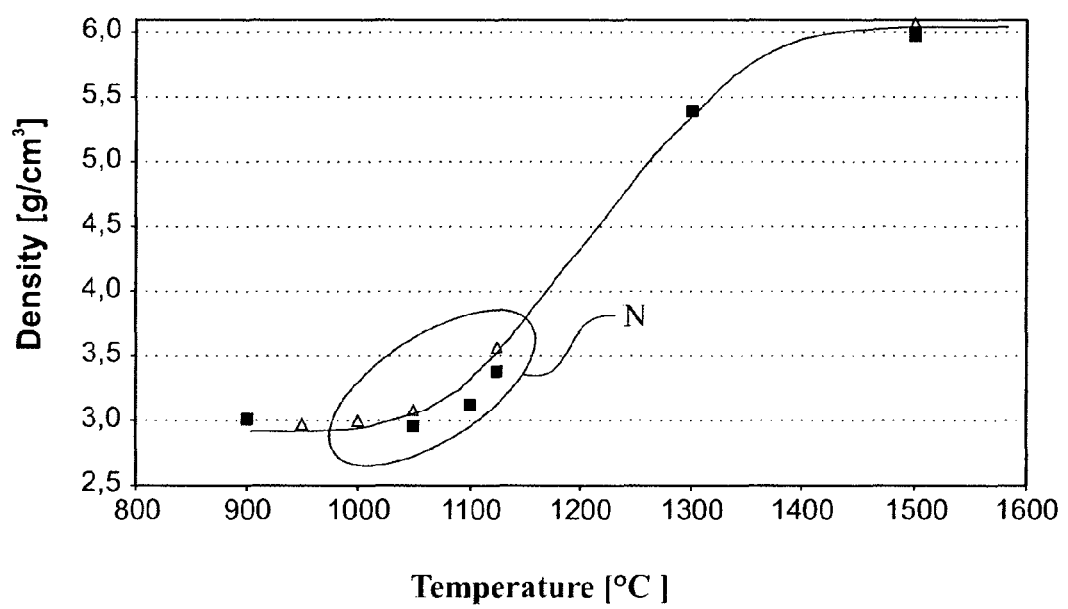
FIG. 7 shows density as a function of temperature for certain embodiments when a green body is subjected to pre-sintering.

Reference will now be made to FIG. 7. FIG. 7 shows the density of the blank 1 in certain embodiments as a function of the temperature used during pre-sintering. For all examples indicated in FIG. 7, the maximum pre-sintering temperature was held for about 2 hours. As previously explained, the temperature increases relatively slowly and the time needed to reach the desired temperature is not included in the 2 hours mentioned. The total time for the pre-sintering process may actually be several hours longer. As shown in FIG. 7, there is a certain part of the temperature range where the density starts to rise sharply. The curve forms a distinctive "neck" N where a relatively flat part of the curve is followed by a sharply rising curve. In certain embodiments, the density of the blanks 1 is closely linked to the strength; with increasing density, also the strength will tend to increase. A consequence of the sharp neck N is that, when the temperature rises over and beyond the temperature in the area of the neck N, the resulting density of the blanks may be more sensitive to small differences in the furnace temperature. For this reason, small differences in temperature between different parts of one and the same blank may result in markedly different density in different parts of the blank. If several blanks 1 are placed in the furnace, temperature differences in the furnace 3 may also have the result that different blanks obtain different density. It should be noted that density cannot simply be equated with strength since blanks with the same density may nevertheless have different strength. However, differences in density during pre-sintering usually correspond to differences in strength. Therefore, it is desirable that the density in certain embodiments should be as uniform as possible. In order to obtain a uniform density in these embodiments, the pre-sintering should be performed at a temperature at the beginning of the area of the neck N, before the curve starts to rise steeply.

It should be noted that the precise location of the neck N may depend on factors such as, for example, material, pre-sintering time, and the pressure used in the making of the green body 2. For example, in some cases good results could be obtained in the range of 970° C.-1150° C. and in some cases 1050° C.-1120° C. as can also be deducted from FIG. 7. When pre-sintering was performed at 1050° C.-1120° C., the resulting blanks had a density in the range of 3.0 g/cm$^3$-3.5 g/cm$^3$. Depending on the exact conditions, suitable blanks may be produced that have a density in the range of 2.9 g/cm$^3$-3.8 g/cm$^3$. Although the density cannot be automatically linked to strength, it has been found that for certain embodiments, density at this stage can give a good indication of the strength. For this reason, it may be suitable to perform the pre-sintering under the conditions indicated above. After machining, the blanks can be sintered to their final density which may be, for example, in the range of 6.00 g/cm$^3$-6.09 g/cm$^3$.

In certain embodiments, the use of blanks having a strength in the indicated ranges will contribute to an effective machining operation. This also means that precision in the manufacturing process can be improved. In certain embodiments, if the pre-sintering is performed at a temperature below 1070° C., it is possible to obtain a more uniform density and strength for the blanks. This is also beneficial during subsequent final sintering when it is important that shrinking can be accurately predicted and calculated before sintering. In many cases, if the blanks are uniform in density, it will be easier to calculate shrinking in advance.

In certain embodiments, the use of one or several retaining sections that extend from a support body to the bridge structure will also contribute to improved precision in the manufacturing process since the retaining section(s) will hold the bridge structure in position during final sintering while the blank is resting on the support body.

All values of strength data mentioned above relates to results obtained by using the punch on three ball test as specified in ISO 6872. More particularly the bending strength relates to the biaxial bending strength of a sample when nothing else is stated in the present document.

Various embodiments of the present invention have been described above. Although this invention has been described with reference to these specific embodiments, the descriptions are intended to be illustrative of the invention and are not intended to be limiting. Various modifications and applications may occur to those skilled in the art without departing from the true spirit and scope of the invention as defined in the appended claims.

What is claimed is:

1. A method of producing a dental product, the method comprising the steps of: providing a blank made from a green body of ceramic material, performing a machining operation on the blank, and subsequently sintering the blank to its final density in a sintering operation performed at a temperature in the range of 1300° C. to 1650° C., and wherein the blank that is provided has a bend strength in the range of 53-74 MPa, and wherein during the machining operation, the blank is machined into a bridge structure and a support body that is linked to the bridge structure by several retaining sections that extend from the support body to the bridge structure, the blank machined to a shape where the bridge structure forms an arch and at least some of the retaining sections are shaped as spokes that extend from a common hub in the support body to the bridge structure, and during the sintering of the blank to its final density, the several retaining sections hold the bridge structure connected to the support body.

2. A method according to claim 1, wherein the blank has a bend strength in the range of 56-65 MPa.

3. A method according to claim 1, wherein the blank has a bend strength in the range of 56-65 MPa in its pre-sintered condition.

4. A method according to claim 1, wherein the blank has a density in the range of 2.9 g/cm$^3$-3.80 g/cm$^3$ in its presintered condition.

5. A method according to claim 1, wherein the blank has a density in the range of 3.0 g/cm$^3$-3.5 g/cm$^3$ in its presintered condition.

6. A method according to claim 1, wherein the blank has been made of a green body of zirconium oxide that has been isostatically pressed and wherein pre-sintering of the green body is performed at a temperature in the range of 970° C.-1150° C.

7. A method according to claim 6, wherein the pre-sintering is performed at a temperature in the range of 1050° C.-1120° C.

8. A method according to claim 1, wherein prior to pre-sintering, the green body blank has been isostatically pressed at a pressure of 200 MPa-300 MPa.

9. A method according to claim 1, wherein after machining, the blank is sintered to a final density of 6.00 g/cm$^3$-6.09 g/cm$^3$.

* * * * *